(12) United States Patent
Ranford

(10) Patent No.: US 6,595,931 B2
(45) Date of Patent: Jul. 22, 2003

(54) FLUID COLLECTION HOLDER

(75) Inventor: Alan B. Ranford, Creve Coeur, MO (US)

(73) Assignee: Sherwood Services AG, Schaffhausen (CH)

( * ) Notice: Subject to any disclaimer, the term of this patent is extended or adjusted under 35 U.S.C. 154(b) by 153 days.

(21) Appl. No.: 09/778,126

(22) Filed: Feb. 5, 2001

(65) Prior Publication Data

US 2002/0107488 A1 Aug. 8, 2002

(51) Int. Cl.$^7$ .................................................. A61B 5/00
(52) U.S. Cl. .................................... 600/573; 604/192
(58) Field of Search ............................... 600/573–583; 604/192–200, 239–245

(56) References Cited

U.S. PATENT DOCUMENTS

| | | | |
|---|---|---|---|
| 4,507,117 A | 3/1985 | Vining et al. | |
| 4,650,468 A | 3/1987 | Jennings, Jr. | |
| 4,675,005 A | 6/1987 | DeLuccia | |
| 4,692,156 A | 9/1987 | Haller | |
| 4,507,117 A | 6/1988 | Vining et al. | |
| 4,892,107 A | * 1/1990 | Haber | 600/576 |
| 4,895,147 A | * 1/1990 | Bodicky et al. | 606/182 |
| 5,030,209 A | 7/1991 | Wanderer et al. | 604/198 |
| 5,070,885 A | 12/1991 | Bonaldo | |
| 5,120,311 A | 6/1992 | Sagstetter et al. | |
| 5,219,333 A | 6/1993 | Sagstetter et al. | |
| 5,300,038 A | 4/1994 | Haber et al. | 604/187 |
| 5,554,130 A | * 9/1996 | McDonald et al. | 604/198 |
| 5,607,402 A | * 3/1997 | Dufresne et al. | 604/265 |
| RE35,539 E | 6/1997 | Bonaldo | |
| 5,685,862 A | 11/1997 | Mahurkar | 604/194 |

FOREIGN PATENT DOCUMENTS

| | | | |
|---|---|---|---|
| EP | 0 539 634 A1 | 5/1993 | A61M/5/32 |
| WO | WO 92/20281 | 11/1992 | A61B/5/14 |

* cited by examiner

*Primary Examiner*—Max F. Hindenburg
*Assistant Examiner*—Pamela Wingood
(74) *Attorney, Agent, or Firm*—Mark S. Leonardo; Brown Rudnick Berlack Israels LLP

(57) ABSTRACT

A fluid collection apparatus is provided that includes a housing and a slide that is moveably supported by the housing. The slide has a cannula tab adapted to support a double ended needle and a plurality of connected segments that are moveably extending therefrom. Proximal movement of the slide causes the plurality of segments to contract in a configuration forming a shield about a proximal end of the double ended needle. The housing may define a slot in an outer surface thereof that is configured to receive a portion of the slide for guiding movement. The cannula tab can include a boss disposed adjacent a distal portion of the slide having the double needle mounted thereto. The cannula tab may include a segment member having a button mounted thereto which is disposed within at least a portion of the slot and slideably engages the slot to facilitate movement of the slide. The plurality of segments can include an end portion extending from a proximal end thereof. The end portion is disposed within a portion of the slot and cooperatively engages the slot to facilitate contraction of the plurality of segments.

22 Claims, 7 Drawing Sheets

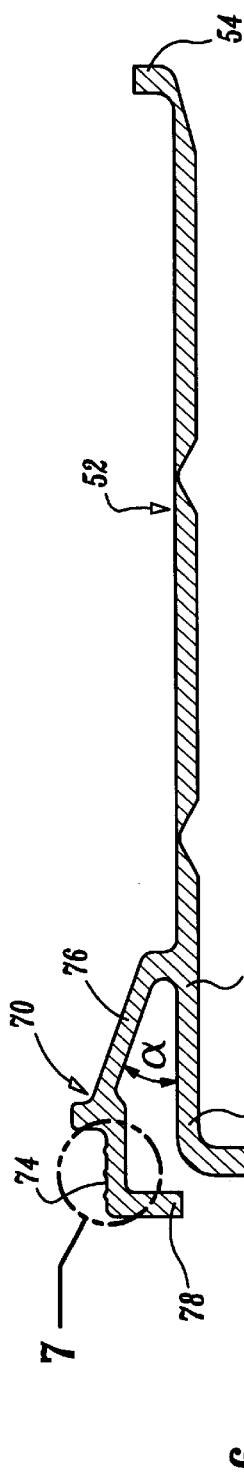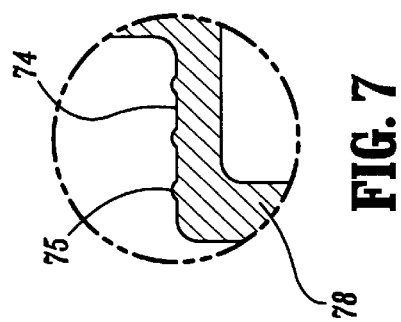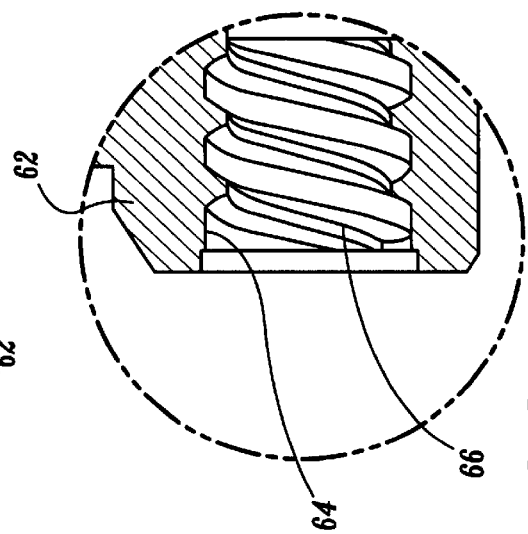
FIG. 5
FIG. 6
FIG. 7

FLUID COLLECTION HOLDER

BACKGROUND

1. Technical Field

The present disclosure generally relates to the field of fluid collection holders employed with fluid collection tubes, and more particularly, to a blood collection holder configured to shield both ends of a double needle cannula.

2. Description of the Related Art

Medical and dental syringes exposed to the AIDS virus or any number of infectious diseases, contaminants, etc., can present serious safety hazards to practitioners, due to accidental contact with needles. A particular danger exists during attachment and removal of a needle from a fluid collection holder, syringe, etc. A number of different devices have been proposed to minimize the possibility of spreading infectious disease due to accidents of this type. One type of medical device uses a needle which is retained in a retracted position after the needle is used to guard against accidental sticks. See, for example, U.S. Pat. Nos. 4,650,468; 4,675,005; 4,692,156; and 4,507,117. These devices are generally of the hypodermic syringe type having a single needle point.

Conventional blood collection procedures involve, such as, for example, venipuncture to draw blood into a blood collection tube, such as, test tubes, etc. The devices used typically include a double ended cannula or needle mounted to one end of a housing that supports the double ended needle. The double ended needle is covered by a protective guard prior to use.

The conventional double ended needle includes a hub having a distal needle portion extending in one direction and a proximal needle portion extending in the other direction. The hub of the double ended needle is threadably engaged with a threaded aperture of the housing supporting the double ended needle. The other end of the housing is open to receive the evacuated blood collection tube which has a stopper to penetrably receive the proximal needle portion. During the procedure, blood flows through the double ended needle into the test tube and can be repeated for several blood collection tubes.

Prior to blood withdrawal, the protective guard is removed and the distal needle portion of the double ended needle is uncovered for insertion into the patient's vein. Typically, after use, the double ended needle is capped with the protective guard or the double ended needle can be retracted within the housing. However, these devices require the user to use both hands to cap the double ended needle or retract the double ended needle within the housing after use. These designs are relatively complicated and time consuming in use. Furthermore, these types of devices present packaging problems for shipping due to their configuration, adding to the costs of manufacture.

Accidental needle stick may be encountered with manipulation of the blood collection device during detachment, replacement or installation of the double ended needle. Inadvertent sticking may also occur during loading and unloading of the blood collection tube with the housing.

Various devices have been developed to minimize the likelihood of inadvertent needle stick from either the distal needle portion or the proximal needle portion. U.S. Reissue Pat. No. 35,539 shows a retractable double ended needle that prevents inadvertent sticking on the proximal needle portion by closing a cap door attached to the rear end of the housing. Another attempt at preventing inadvertent sticking of a double ended needle is disclosed in Denmark Application WO 90/02515, showing a movable protective member that engages a cam projecting from an inner surface of a holder for blocking the proximal needle portion of the double ended needle. These types of devices, however, may not provide uniform and reliable motion as the protective member and the cam tend to jam or move offline, resulting in faulty operation and a dangerous condition to the user.

Therefore, it would be desirable to have a fluid collection apparatus having a shielding capability that protects the user from the ends of a double ended needle by forming a protective configuration about the ends of the double ended needle during operation of the fluid collection apparatus. Desirably, the fluid collection apparatus guides movement of its working components to provide dependable performance and increased safety to the user.

SUMMARY

Accordingly, a fluid collection apparatus is disclosed to be employed with evacuated blood collection tubes and double ended blood collection cannulas for drawing blood and/or fluids from patients. The fluid collection apparatus protects a practitioner from both ends of a double ended needle. This and other advantages are accomplished by retraction of a distal end of the double ended needle and a plurality of segments that form a protective configuration about a proximal end of the double ended needle. The fluid collection apparatus guides movement of its working components to provide dependable performance and increased safety to the practitioner during a blood and/or fluid collection procedure.

In one particular embodiment, a fluid collection apparatus is provided, in accordance with the principles of the present disclosure. The fluid collection apparatus includes a housing and a slide that is moveably supported by the housing. The slide has a cannula tab adapted to support a cannula which may include such as, for example, a double ended needle, and a plurality of connected segments that are moveably extending from the slide. Proximal movement of the slide causes the plurality of segments to contract in a configuration forming a shield about a proximal end of the double ended needle. This structure advantageously protects a user from inadvertent needle stick with one-handed operation. The housing may define a slot in an outer surface thereof that is configured to receive a portion of the slide for guiding movement of the slide. The slot can be elongated along a longitudinal axis of the housing facilitating axial movement of the slide in a predetermined manner. This configuration advantageously provides guided movement of the slide.

The cannula tab can include a boss disposed adjacent a distal portion of the slide. The double ended needle is mounted with the boss. The double ended needle may be threadably received by the boss. The cannula tab may include a segment member having a button mounted thereto. The button is disposed within at least a portion of the slot and slideably engages the slot to facilitate movement of the slide. Alternatively, the segment member includes a transverse portion having the double ended needle mounted therewith. The transverse portion is configured to spatially orient projection of the double ended needle from the housing.

The plurality of segments can include an end portion extending from a proximal end thereof. The end portion is disposed within a portion of the slot and cooperatively engages the slot to facilitate contraction of the plurality of segments. The plurality of segments may include at least one planar surface. Desirably, the plurality of segments are connected by hinges for relative movement. Most desirably, the slide has a range of movement including a distal position whereby a distal end of the double ended needle extends outside of the housing and a proximal position whereby the distal end of the double ended needle is retracted within the housing. The button may releasably lock the slide in the distal position.

In an alternate embodiment, the fluid collection apparatus includes a shield that extends from the cannula tab and an end portion that extends from the shield. The end portion is moveably disposed within at least a portion of the slot of the housing such that proximal movement of the slide causes the end portion to engage the slot so that the shield forms a protective configuration about a proximal end of the cannula. The shield may include a plurality of connected segments moveably extending from the cannula tab. The cannula tab may include a longitudinal portion having a button mounted thereto. The button is disposed within at least a portion of the slot and slideably engages the slot to facilitate movement of the slide.

In another alternate embodiment, a blood collection apparatus is provided that includes a housing defining an axially elongated slot in an outer surface thereof. A slide is moveably supported by the housing and includes a double ended needle tab, a shield and an end portion. The double ended needle tab has a segment member having a longitudinal portion that is axially aligned with the slot of the housing. The longitudinal portion has a button mounted thereto and the transverse portion has a boss adapted to threadably secure a double ended needle therewith. The button is moveably disposed within a portion of the slot and cooperatively engages the slot to facilitate movement of the slide.

The shield includes a plurality of planar segments that moveably extend from the double ended needle tab whereby the plurality of planar segments are connected by flexible hinges. The end portion extends from a proximal end of the shield. The end portion is disposed within a portion of the slot and cooperatively engages the slot.

The slide has a range of movement between a distal position whereby a distal end of the double ended needle extends outside of the housing and a proximal position whereby the distal end of the double needle is retracted within the housing. Proximal movement of the slide is facilitated by manipulation of the button causing the end portion to engage the housing at a distal position limit, causing the plurality of planar segments of the shield to contract in a substantially V-shaped configuration, forming a shield about a proximal end of the double ended needle.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings wherein:

FIG. 5 is a side cross-sectional view of the slide shown in FIG. 4 taken along lines 5—5;

FIG. 6 is an enlarged cross-sectional view, in part elevation, of the indicated area of detail shown in FIG. 5;

FIG. 7 is an enlarged cross-sectional view of the indicated area of detail shown in FIG. 5;

DETAILED DESCRIPTION OF EXEMPLARY EMBODIMENTS

The exemplary embodiments of the fluid collection apparatus and methods of operation disclosed are discussed in terms of fluid collection procedures, and more particularly, in terms of blood collection holders employing a double ended needle cannula having both ends shielded to prevent inadvertent needle stick. It is contemplated that the needle cannula ends may be shielded during use including transport, between tube filling, subsequent to a fluid collection procedure, etc. It is envisioned, however, that the present disclosure finds applications to a wide variety of cannula needles and syringe components for collection of bodily fluids, including, those employed during procedures relating to phlebotomy, dental, orthopedic, digestive, intestinal, urinary, veterinary types, etc. It is also envisioned that the present disclosure finds application to the injection of preventive medications, medicaments, etc., to a subject.

In the discussion which follows, the term "proximal" will refer to the portion of a structure which is closer to the practitioner, while the term "distal" will refer to the portion which is further from the practitioner. As used herein, the term "subject" refers to a patient which receives injections or has blood and/or other fluids collected therefrom using the fluid collection apparatus. According to the present disclosure, the term "practitioner" refers to an individual administering an injection, performing fluid collection, installing or removing a needle cannula from a syringe using the fluid collection apparatus and may include support personnel.

The following discussion includes a description of the fluid collection apparatus, followed by a description of the methods of operating the fluid collection apparatus in accordance with the present disclosure. Reference will be now be made in detail to the exemplary embodiments of the disclosure, which are illustrated in the accompanying figures.

Figure 1:
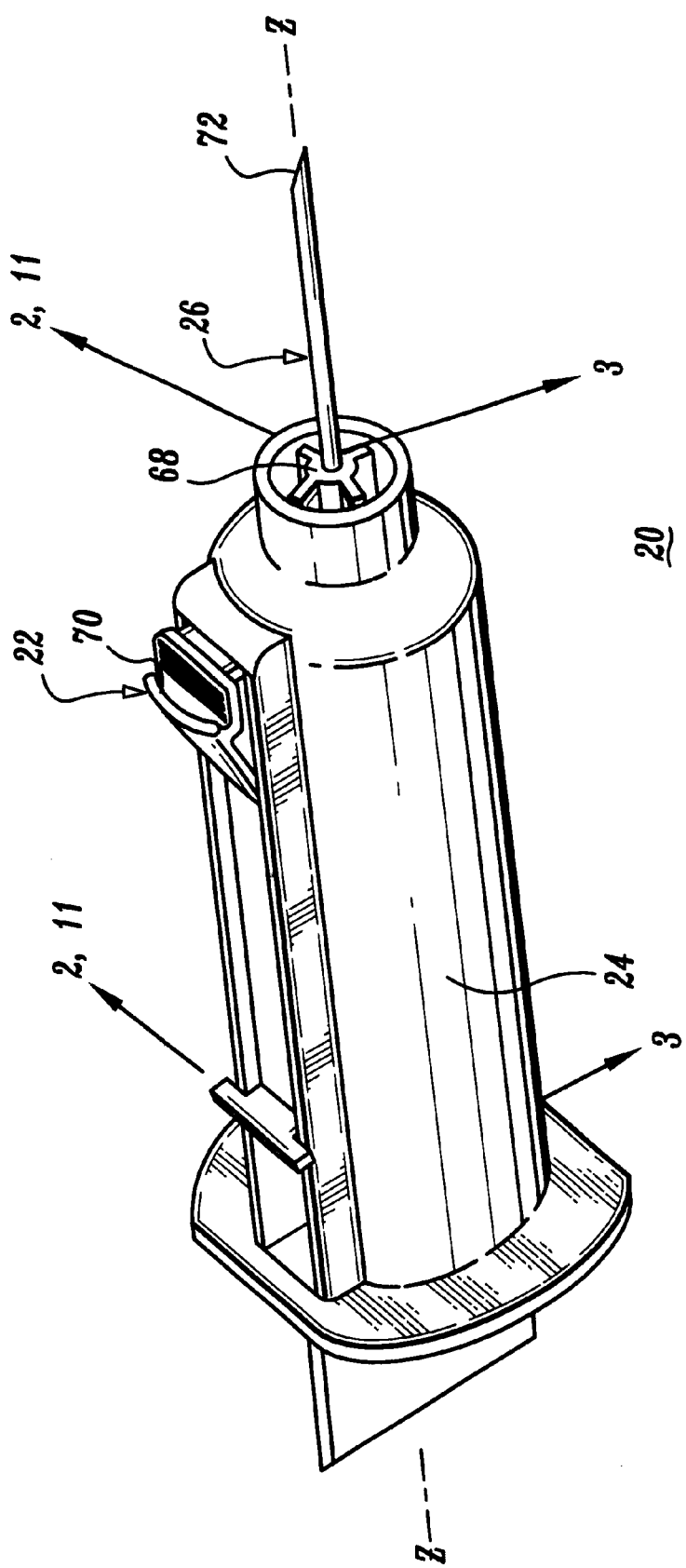
FIG. 1 is a perspective view of one embodiment of a fluid collection apparatus, shown in cutaway, in accordance with the principles of the present disclosure.
Figure 2:
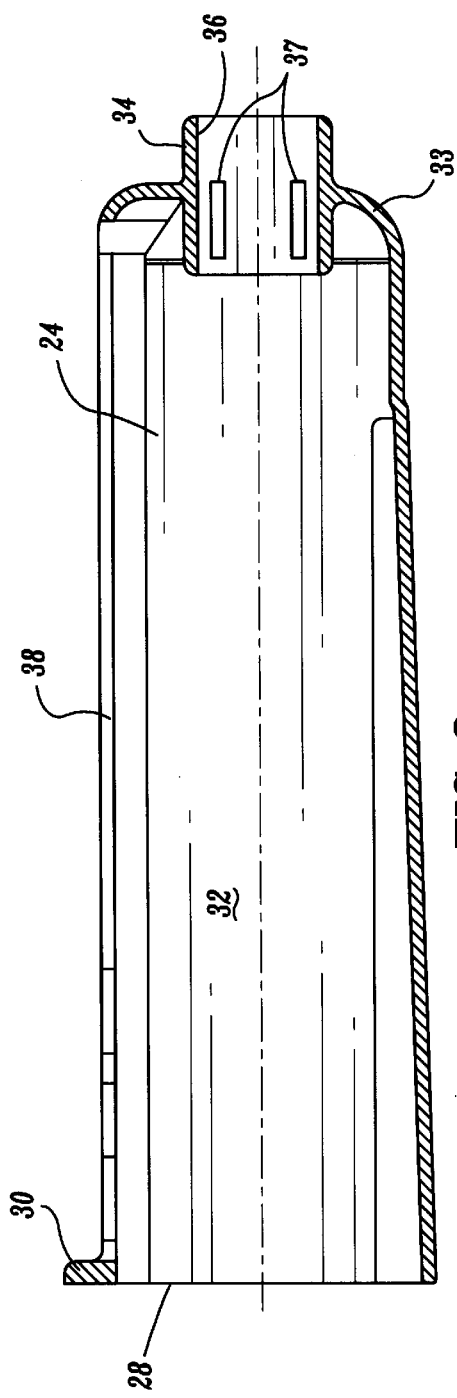
FIG. 2 is a side cross-sectional view of a housing of the fluid collection apparatus shown in FIG. 1 taken along the lines 2—2.
Figure 3:
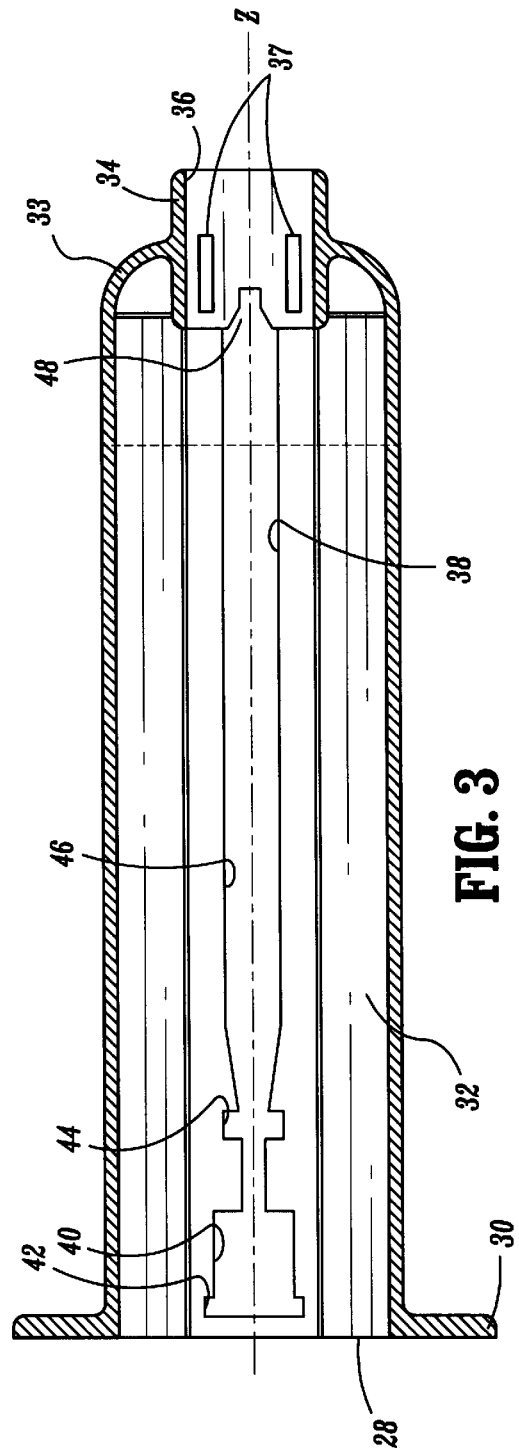
FIG. 3 is a top cross-sectional view, in part elevation, of the housing of the fluid collection apparatus shown in FIG. 1 taken along lines 3—3.

Turning now to the figures wherein like components are designated by like reference numerals throughout the several views. Referring initially to FIGS. 1–3, there is illustrated a fluid collection apparatus 20, constructed in accordance with the principles of the present disclosure, which includes a slide 22 being movably supported by an axially elongated cylindrical housing 24. Slide 22 is adapted to support a cannula, such as, for example, a double ended blood collection needle 26. It is contemplated that other cannulas which define a lumen for passage of fluids, such as, for example, syringes, etc., may be employed with fluid collection apparatus 20. It is envisioned that housing 24 may have other cross-sectional configurations, such as, for example, rectangular, elliptical, etc.

Fluid collection apparatus 20, manufactured by Kendall Healthcare Products of Mansfield, Mass., is contemplated for use in the field of blood collection. More particularly, Kendall's fluid collection apparatus 20 is envisioned to be a single use, disposable blood collection safety apparatus employing such safety features as shielding capabilities to prevent inadvertent sticking or punctures of medical personnel, one hand operation, uniform and dependable movement of slide 22 during a procedure and a locking mechanism for reliable use. The above advantages, among others realized from the present disclosure, are attained through the disclosed fluid collection apparatus 20 which includes a plurality of connected segments that form a protective configuration about a proximal needle point of double ended needle 26 and slideable engagement of housing 24 and slide 22, facilitating uniform and dependable motion thereof, as discussed herein below. These features of the present disclosure advantageously facilitate a safe collection of body fluids and prevent inadvertent needle stick of the practitioner.

Referring to FIGS. 2 and 3, housing 24 is substantially tubular and constructed of a resilient material, such as molded medical grade polypropylene, although, other semi-rigid and rigid polymerics may be used. It is envisioned that the cylindrical walls of housing 24 have an approximate thickness in the range of 1 to 2 tenths of an inch, although, other thicknesses are envisioned depending on the particular medical application.

It is contemplated that housing 24 may be integrally assembled of its constituent components from a material suitable for fluid collection applications, such as, for example, polymerics or metals, such as stainless steel, depending on the particular medical application and/or preference of a user. One skilled in the art, however, will realize that other materials and fabrication methods suitable for assembly and manufacture, in accordance with the present disclosure, also would be appropriate.

Housing 24 includes a proximal open end 28 having a flange 30 formed thereabout to provide stability during operation. Housing 24 may also be constructed without flange 30. A longitudinal passage 32 is defined by an inner surface of housing 24 extending from proximal open end 28 to a distal end 33 of housing 24. Longitudinal passage 32 facilitates receipt of the components of fluid collection apparatus 20. A boss 34 is formed adjacent distal end 33 and includes an aperture 36 having notches 37 configured for aligning a hub 68 (FIG. 1), discussed below.

An elongated slot 38 is defined within an outer surface of housing 24 and is configured to receive slide 22 (FIG. 1) for guiding movement thereof along a longitudinal axis Z defined by housing 24. The sliding engagement of slide 22 within slot 38 advantageously provides uniform and dependable movement of the constituent parts of fluid collection apparatus 20. Slot 38 extends axially along a substantial portion of housing 24 forming a track configuration with slide 22 for axial movement of slide 22 therealong.

Slot 38 includes an end cavity 40 having a stop portion 42 defined adjacent proximal open end 28 of housing 24. From end cavity 40, slot 38 extends distally and communicates with a retraction lock cavity 44 whereby double ended needle 26 is locked in a proximal position due to engagement of slide 22 with slot 38, discussed hereinbelow. From retraction lock cavity 44, slot 38 extends distally, being configured as a longitudinal opening 46, and communicates with extended lock cavity 48 whereby double ended needle 26 is locked in a distal position. The surfaces of slot 38 and their respective engagement with particular portions of slide 22 will be discussed in greater detail below. It is contemplated that slot 38 may extend along housing 24 in various orientations, such as, for example, laterally, spiral, etc. It is also contemplated that slot 38 may only extend along a portion of housing 24.

Figure 4:
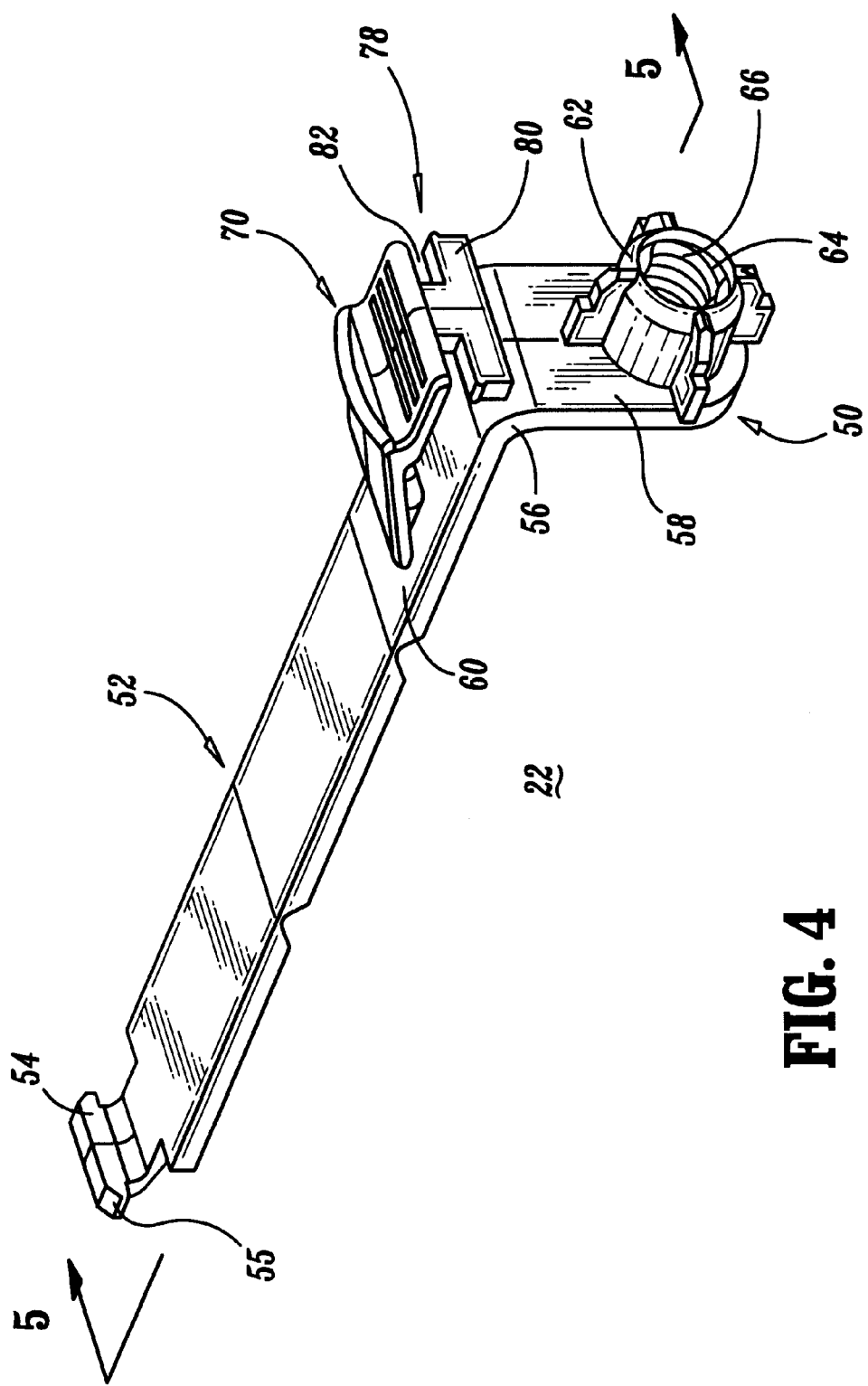
FIG. 4 is a perspective view of a slide of the fluid collection apparatus shown in FIG. 1.

Referring to FIG. 4, slide 22 includes a cannula tab, such as, for example, a double needle tab 50, a shield 52 and an end portion 54. Double needle tab 50 includes an angled segment member 56 having a transverse portion 58 oriented at a 90° angle from a longitudinal portion 60. The angled configuration of segment member 56 advantageously facilitates alignment of slide 22 with housing 24 such that longitudinal portion 60 is axially aligned with slot 38 for axial movement of slide 22 therealong. Moreover, transverse portion 58 is oriented at a 90° angle from longitudinal portion 56 such that double ended needle 26 is substantially coaxial with housing 24 so that double ended needle 26 effectively projects from fluid collection apparatus 20 for a fluid collection procedure. It is contemplated that transverse portion 58 may be oriented at other angles according to the particular medical application and/or preference of a user.

Double needle tab 50 includes a boss 62 mounted with transverse portion 58 adjacent a distal portion of slide 22. Boss 62 may be monolithically formed or integrally assembled with transverse portion 58 by, for example, threading, adhesives, etc. Referring to FIGS. 5 and 6, boss 62 is adapted for threadably securing double ended needle 26 within an aperture 64 defined on an inner surface thereof. The inner surface defines threads 66 for threadably receiving a threaded portion of the hub 68 (FIG. 1) of double ended needle 26. It is contemplated that double ended needle 26 may be mounted with slide 22 by alternative means, such as, for example, press fit, friction fit, or integral with slide 22.

Referring now to FIGS. 5 and 7, longitudinal portion 60 of angled segment member 56 has a button 70 mounted thereto. Button 70 is configured for disposal within slot 38 (FIG. 3) and slideably engages slot 38 to facilitate movement of slide 22. Button 70 may be monolithically formed with slide 22 or integrally assembled therewith by adhesives, clips, etc. Button 70 is mounted to longitudinal portion 60 to facilitate axial manipulation and releasable locking of slide 22.

Button 70 is manipulable for a range of movement of slide 22 between a distal position (FIG. 1) whereby a distal needle point 72 of double ended needle 26 extends outside of housing 24 and a proximal position (FIG. 8) whereby distal needle point 72 is retracted within housing 24. Although shown as a manually manipulated fluid collection apparatus 20, it is contemplated that the movement of slide 22 relative to housing 24 may be controlled through motorized mechanisms, electronic components, etc.

Button 70 is ergonomically designed for manipulation by a practitioner. Button 70 includes a finger pad 74 facilitating effective gripping of button 70 during manipulation of slide 22. Finger pad 74 includes a plurality of spaced apart elongated projections 75 that allow a practitioner to grip button 70. This advantageously provides a reliable method of extension and retraction of double ended needle 26 during a blood collection procedure.

Button 70 includes a resilient arm 76 oriented at an angle α from longitudinal portion 60. Angle α represents a range of motion and corresponding displacement of button 70 when radially inwardly depressed to unlock slide 22 from the distal and proximal positions. Arm 76 is constructed from a material having sufficient resilient characteristics such that subsequent to depression, button 70 is biased to its original position, i.e., arm 76 returns to angle α relative to longitudinal portion 60. It is contemplated that arm 76 may be constructed from a material different from slide 22 or, alternatively, have a reduced thickness adjacent the connection area of arm 76 and slide 22 to provide elasticity during manipulation of arm 76. It is envisioned that angle α may be altered depending on the degree of radially inward travel necessary to effect releasable engagement of button 70 with slide 22.

Button 70 includes a latch 78 for effecting releasable engagement of button 70 with slot 38 (FIG. 3). Latch 78 includes a stop 80 and a pair of slots 82 (FIG. 4). Stop 80 facilitates locking of slide 22 in the proximal and distal positions. This feature of the present disclosure advantageously prevents axially directed movement of slide 22 by engagement of stop 80 with retraction lock cavity 44 and extended lock cavity 48. Slots 82 facilitate relative movement of slide 22 therein by slideable engagement with the surfaces of slot 38, including longitudinal opening 46.

Figure 9:
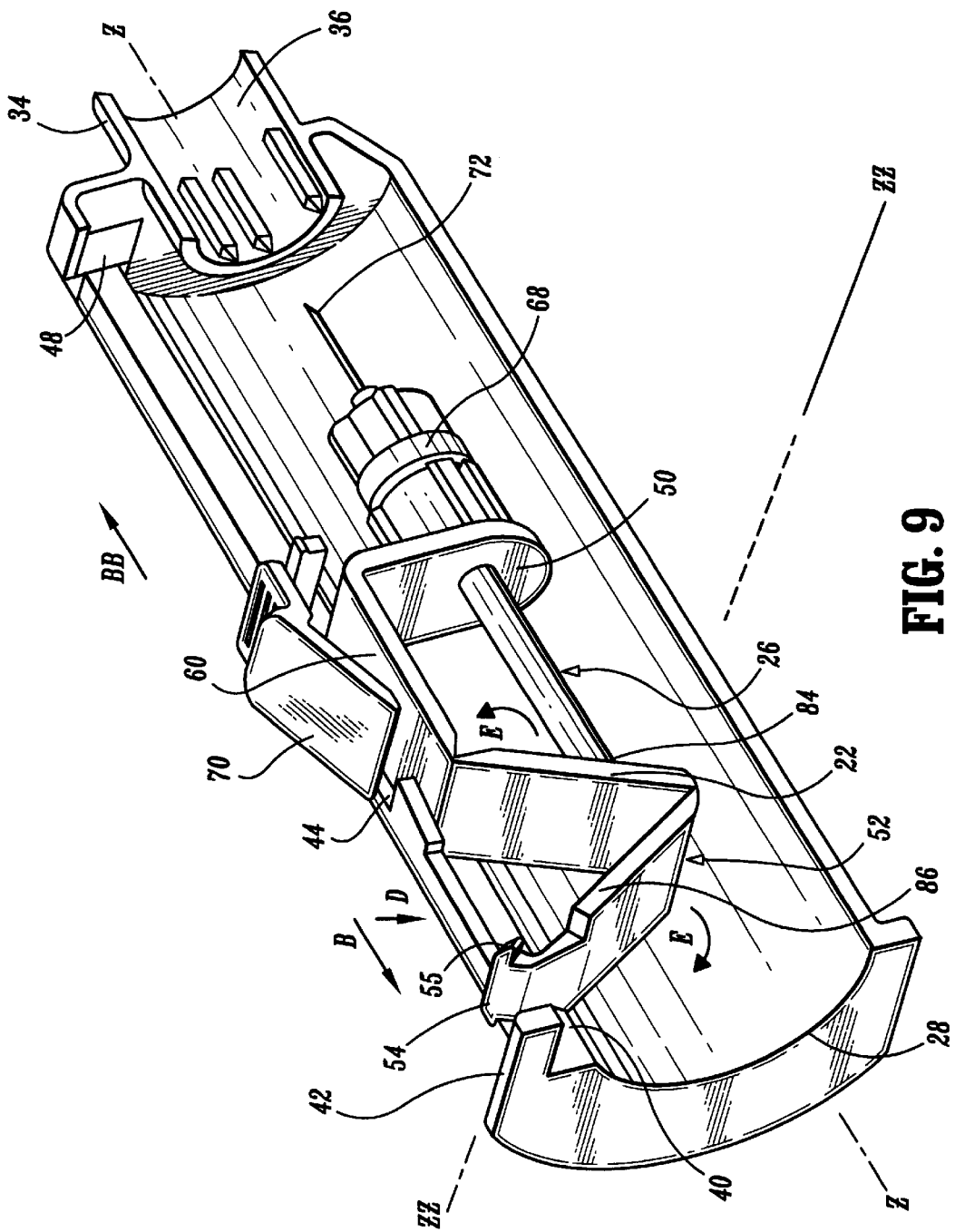
FIG. 9 is a perspective view of the fluid collection apparatus shown in FIG. 1, having the half removed and the slide between the proximal and a distal position.
Figure 10:
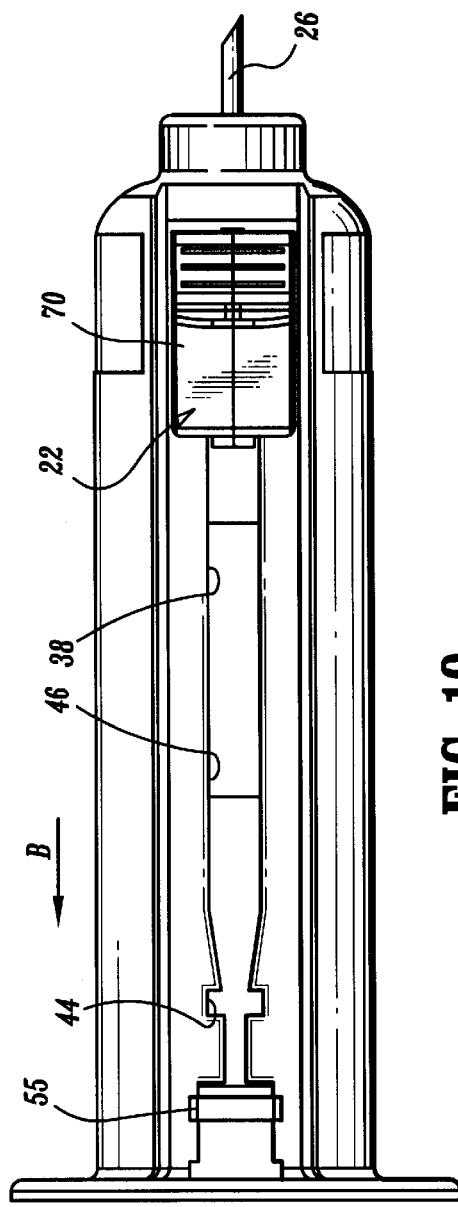
FIG. 10 is a top plan view of the fluid collection apparatus shown in FIG. 1.
Figure 11:
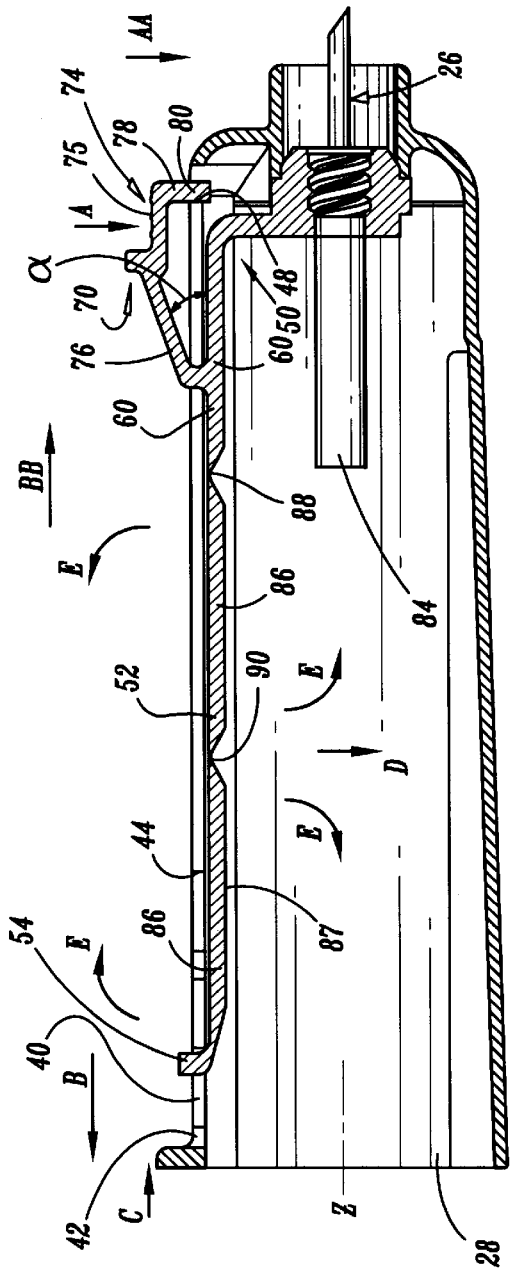
FIG. 11 is a side cross-sectional view, in part elevation, of the fluid collection apparatus shown in FIG. 1 taken along lines 11—11.

Referring to FIGS. 9–11, the range of movement between the distal and proximal positions will now be described. As shown in FIGS. 10 and 11, slide 22 is initially disposed in the distal position whereby slide 22 is releasably locked by the locking engagement of stop portion 80 with the surfaces of extended lock cavity 48 thereby preventing proximal movement of slide 22. The practitioner grasps fluid collection apparatus 20 with one hand (not shown) and using, for example, an extended finger or a thumb of the hand, applies a manual force A, in the direction of the arrow shown, to finger pad 74. Projections 75 of finger pad 74 allow the extended finger of the hand to effectively grip button 70. This feature advantageously prevents accidental slipping of fluid collection apparatus 20 during manipulation thereby avoiding a dangerous condition including inadvertent needle stick to a practitioner from double ended needle 26.

Manual force A causes latch 78 of button 70 to travel radially inward, in the direction shown by arrow AA. Angle α between arm 76 and longitudinal portion 60 is reduced until stop 80 travels such that stop 80 sufficiently clears the surfaces of slot 38 and, in particular, the surfaces of extended lock cavity 48. This releases button 70 from locking engagement with slot 38.

Figure 8:
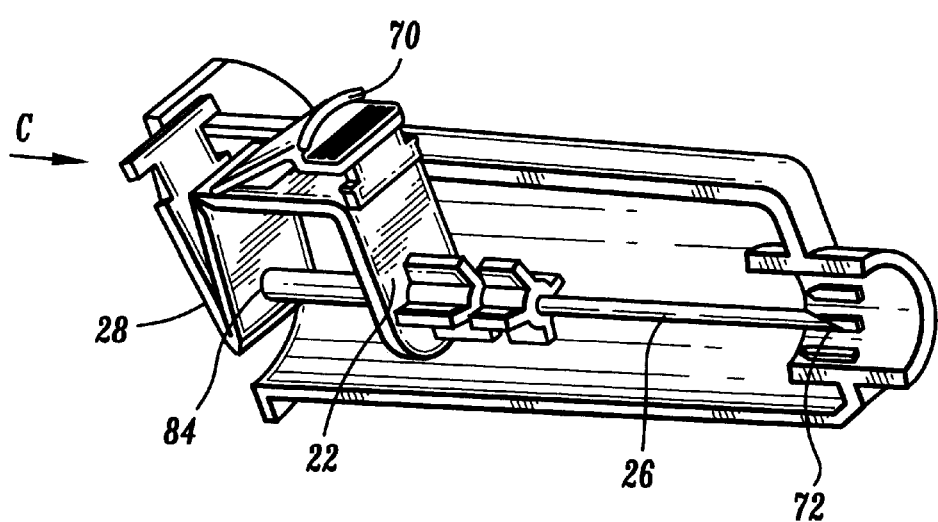
FIG. 8 is a perspective view of the fluid collection apparatus shown in FIG. 1 with a half removed and the slide in a proximal position.

With stop 80 cleared, slots 82 (clearly shown in FIG. 4) are free to axially travel in the proximal direction. The extended finger of the hand manipulates button 70 along slot 38 of housing 24, in the direction shown by arrow B, such that longitudinal opening 46 of slot 38 is slideably engaged by slots 82. This engagement causes slide 22 to axially travel along slot 38 until latch 78 is disposed within retraction lock cavity 44 and the proximal position is reached, as shown in FIG. 8. The extended finger of the hand disengages finger pad 74 of button 70 and arm 76 resiliently biases radially outward until arm 76 is oriented back to angle α from longitudinal portion 60 within retraction lock cavity 44 of slot 38.

Stop 80 travels a sufficient distance to engage the surfaces of retraction lock cavity 44 such that distal movement of slide 22 is prevented. Button 70 is in locking engagement with slot 38 and correspondingly, slide 22 is locked with housing 24 in the proximal position. It is envisioned that slide 22 may be manipulated, similar to that described above, distally in the direction shown by arrow BB.

As slide 22 axially moves toward and becomes locked in the proximal position, shield 52 forms a protective configuration about a proximal needle point 84 of double ended needle 26. Shield 52 includes a plurality of planar segments 86 moveably extending from double needle tab 50. Planar segments 86 have a rectangular configuration and planar surfaces 87 to advantageously form a protective shield about proximal needle point 84 of double ended needle 26 in the proximal position. It is envisioned that planar segments 86 may have other configurations, such as, for example, circular, polygonal, etc., or convex, concave, etc. Planar segments 86 are connected to longitudinal portion 60 of cannula tab 50 by a hinge 88. Hinge 88 facilitates movement of planar segments 86 relative to double needle tab 50. Similarly, planar segments 86 are connected by a hinge 90 to facilitate relative movement.

Hinges 88 and 90 are flexible members facilitating relative movement of the components they connect. Hinges 88 and 90 may be monolithically formed by a reduced thickness of planar segments 86, heat-treating, etc., or alternatively, may be separate members that are integrally assembled with the components they connect. End portion 54 is monolithically formed with planar segment 86. It is contemplated that end portion 54 may be separately formed and integrally assembled with planar segment 86.

In the distal position, planar segments 86 are axially aligned relative to slot 38. It is envisioned that, in the distal position, planar segments 86 may sag downward, rest on double ended needle 26, etc., depending on the materials of fabrication used, component dimensions, needle application, etc. End portion 54 is disposed within a distal portion of end cavity 40 of slot 38. End portion 54 has a T-shaped configuration which includes slot arms 55 (shown clearly in FIG. 4). Slot arms 55 engage a top surface of housing 24 adjacent slot 38 to advantageously facilitate guided travel of end portion 54 within end cavity 40. Slot arms 55 rest on the top surface of housing 24 in sliding engagement during axial movement of slide 22.

Referring to FIG. 9, as slide 22 moves axially, from the distal position to the proximal position, described above, in the direction shown by arrow B, end portion 54 slideably engages the surfaces of end cavity 40 in the proximal direction. Correspondingly, slot arms 55 slide along the top surface of housing 24. End portion 54 simultaneously moves in a proximal direction with slide 22 until a proximal limit, such as, for example, stop 42 is reached. End portion 54 engages stop 42 and ceases axial proximal movement, while manipulation and proximal movement of slide 22, in the direction shown by arrow B, continues.

Referring back to FIG. 11, a resistant force C, in the direction of the arrow shown, acts on planar segments 86 causing hinges 88 and 90 to yield such that planar segments 86 flexibly move about a transverse axis ZZ (FIG. 9) relative to longitudinal axis Z of housing 24. Hinge 90 is urged downward, in the direction shown by arrow D, and planar segments 86 are urged to contract and fold, in the direction shown by arrows E, toward a configuration forming a shield about proximal needle point 84 of double ended needle 26. In the proximal position, the protective configuration is fully realized.

The operation of fluid collection apparatus 20 during a medical procedure will now be described. Initially, proper preparation and sterilization of fluid collection apparatus 20 is conducted. Referring to FIG. 1, fluid collection apparatus 20 is initially locked in the distal position, as discussed above. Hub 68 of double ended needle 26 is threadably received by threads 66 of boss 62, as discussed with regard to FIGS. 5 and 6, and a phlebotomy procedure is performed.

After the phlebotomy procedure is completed, button 70 of slide 22 is manipulated with one-handed operation (not shown). An extended finger of the hand engages finger pad 74 of button 70 causing arm 76 to resiliently travel radially inward and reduce angle α, as discussed. Stop 80 of latch 78 moves out of engagement with the surfaces of extended lock cavity 48 of slot 38 releasing button 70 and correspondingly, slide 22 from locking engagement with slot 38 and housing 24. Referring again to FIGS. 9–11, button 70 is manipulated by the extended finger proximally, in the direction shown by arrow B, causing slide 22 to move to the proximal position.

During proximal movement, end portion 54 slideably engages end cavity 40 of slot 38 and travels axially therealong until end portion 54 engages stop 42, as discussed. Continued proximal movement of slide 22, subsequent to engagement of end portion 54 with stop 42, produces resistive force C, in the direction of the arrow shown, causing hinges 88, 90 to yield. This causes planar segments 86 to contract and fold, in the direction shown by arrows E, as hinge 90 is urged downward, in the direction shown by arrow D, forming a protective configuration about proximal needle point 84 of double ended needle 26.

Referring again to FIG. 8, in the proximal position, planar segments 86 form a V-shaped configuration that shields inadvertent access to proximal needle point 84 of double ended needle 26 through proximal opening 28 of housing 24. Further, in the proximal position, distal needle point 72 of double ended needle 26 is retracted within and enclosed by housing 24. This prevents inadvertent needle stick of the practitioner by distal needle point 72. The practitioner is, therefore, protected from accidental needle stick from distal needle point 72 and proximal needle point 84. These features advantageously enable a user to shield the proximal and distal needle points 72 and 84 of double ended needle 26, which may be exposed to infectious diseases, contaminants, etc., with a single handed deployment motion.

It will be understood that various modifications may be made to the embodiments disclosed herein. Therefore, the above descriptions should not be construed as limiting, but merely as exemplifications of the various embodiments. Those skilled in the art will envision other modifications within the scope and spirit of the claims appended hereto.

What is claimed is:

1. A fluid collecting apparatus comprising:
   a housing; and
   a slide being movably supported by the housing, the slide including a cannula tab adapted to support a cannula and a plurality of connected segments movably extending therefrom,
   wherein proximal movement of the slide causes the plurality of segments to contract in a configuration forming a shield about a proximal end of the cannula.

2. The fluid collecting apparatus as recited in claim 1, wherein the housing defines a slot in an outer surface thereof configured to receive a portion of the slide for guiding movement thereof.

3. The fluid collecting apparatus as recited in claim 2, wherein the slot is elongated along a longitudinal axis of the housing facilitating axial movement of the slide in a predetermined manner.

4. The fluid collecting apparatus as recited in claim 1, wherein the cannula tab includes a boss disposed adjacent a distal portion of the slide, the cannula being mounted with the boss.

5. The fluid collecting apparatus as recited in claim 4, wherein the cannula is threadably received by the boss.

6. The fluid collecting apparatus as recited in claim 2, wherein the cannula tab includes a segment member having a button mounted thereto, the button being disposed within at least a portion of the slot and slideably engaging therewith to facilitate movement of the slide.

7. The fluid collecting apparatus as recited in claim 6, wherein the segment member includes a transverse portion having the cannula mounted therewith, the transverse portion configured to orient projection of the cannula from the housing.

8. The fluid collecting apparatus as recited in claim 6, wherein the plurality of segments includes an end portion extending from a proximal end thereof, the end portion being disposed within a portion of the slot and cooperatively engaging therewith to facilitate contraction of the plurality of segments.

9. The fluid collecting apparatus as recited in claim 2, wherein the plurality of segments includes an end portion extending from a proximal end thereof, the end portion being disposed within at least a portion of the slot and cooperatively engaging therewith to facilitate contraction of the plurality of segments.

10. The fluid collecting apparatus as recited in claim 1, wherein the plurality of segments include at least one planar surface.

11. The fluid collecting apparatus as recited in claim 1, wherein the plurality of segments are connected by hinges for relative movement.

12. The fluid collecting apparatus as recited in claim 1, wherein the cannula includes a double ended needle.

13. The fluid collecting apparatus as recited in claim 1, wherein the slide has a range of movement including a distal position whereby a distal end of the cannula extends outside of the housing and a proximal position whereby the distal end of the cannula is retracted within the housing.

14. The fluid collecting apparatus as recited in claim 13, wherein the slide is releasably lockable in the distal position.

15. A fluid collecting apparatus comprising:
    a housing defining a slot in an outer surface thereof; and
    a slide being movably supported by the housing, the slide including a cannula tab adapted to support a cannula, a shield and including a plurality of segments extending from the cannula tab and an end portion extending from the shield,
    wherein the end portion is movably disposed within at least a portion of the slot of the housing such that proximal movement of the slide causes the end portion to engage the slot so that the shield forms a protective configuration about a proximal end of the cannula.

16. The fluid collecting apparatus as recited in claim 15, wherein the shield includes a plurality of connected segments movably extending from the cannula tab.

17. The fluid collecting apparatus as recited in claim 16, wherein the plurality of segments are connected by hinges for relative movement.

18. The fluid collecting apparatus as recited in claim 15, wherein the slide has a range of movement including a distal position whereby a distal end of the cannula extends outside of the housing and a proximal position whereby the distal end of the cannula is retracted within the housing.

19. The fluid collecting apparatus as recited in claim 18, wherein the cannula tab includes a longitudinal portion having a button mounted thereto, the button being disposed within at least a portion of the slot and slideably engaging therewith to facilitate movement of the slide.

20. The fluid collecting apparatus as recited in claim 19, wherein the button releasably locks the slide in the distal position.

21. A blood collection apparatus comprising:
   a housing defining an axially elongated slot in an outer surface thereof; and
   a slide being movably supported by the housing and including a double needle tab, a shield and an end portion,
   the double needle tab has a segment member having a longitudinal portion being axially aligned with the slot of the housing and a transverse portion having a boss adapted to threadably secure a double needle therewith, the longitudinal portion having a button mounted thereto, the button being movably disposed within a portion of the slot and slideably engaging therewith to facilitate movement of the slide,
   the shield including a plurality of planar segments movably extending from the double needle tab whereby the plurality of planar segments are connected by hinges, the end portion extending from a proximal end of the shield, the end portion being disposed within a portion of the slot and cooperatively engaging therewith,
   wherein the slide has a range of movement including a distal position whereby a distal end of the double needle extends outside of the housing and a proximal position whereby the distal end of the double needle is retracted within the housing such that engagement of the end portion with the housing at a proximal position limit causes the plurality of planar segments of the shield to contract in a substantially V-shaped configuration about a proximal end of the double needle.

22. The blood collection apparatus as recited in claim 21, wherein the button is releasably lockable in the distal position.

* * * * *